(12) United States Patent
Hwang et al.

(10) Patent No.: US 8,722,758 B2
(45) Date of Patent: May 13, 2014

(54) WATER SOLUBLE POLYIMIDE RESIN, ITS PREPARATION AND USE

(75) Inventors: Kuen Yuan Hwang, Taipei (TW); An Pang Tu, Taipei (TW); Sheng Yen Wu, Hsinchu Industrial District (TW); Gai Chi Chen, Hsinchu Industrial District (TW); Ching Jui Huang, Hsinchu Industrial District (TW); Jen Fu Wang, Hsinchu Industrial District (TW)

(73) Assignee: Chang Chun Plastics Co., Ltd., Taipei (TW)

( * ) Notice: Subject to any disclaimer, the term of this patent is extended or adjusted under 35 U.S.C. 154(b) by 261 days.

(21) Appl. No.: 13/005,041

(22) Filed: Jan. 12, 2011

(65) Prior Publication Data
US 2011/0172324 A1 Jul. 14, 2011

(30) Foreign Application Priority Data
Jan. 14, 2010 (TW) ................ 99100888 A

(51) Int. Cl.
*C08G 77/10* (2006.01)

(52) U.S. Cl.
USPC ........................................... 522/168

(58) Field of Classification Search
USPC ............. 522/168; 525/434; 528/26; 562/453
See application file for complete search history.

(56) References Cited

U.S. PATENT DOCUMENTS

| 4,321,319 A | 3/1982 | Shoji et al. |
| 5,668,248 A | 9/1997 | Hagiwara et al. |
| 6,001,534 A | 12/1999 | Kato |
| 8,084,512 B2 * | 12/2011 | Wang et al. .................. 522/168 |
| 2010/0167208 A1 * | 7/2010 | Wang et al. ................ 430/287.1 |

* cited by examiner

*Primary Examiner* — Gregory Listvoyb
(74) *Attorney, Agent, or Firm* — Muncy, Geissler, Olds & Lowe, P.C.

(57) ABSTRACT

The present invention relates to a novel water soluble polyimide resin, which contains a hydrophilic functional group such as —OH, —COOH to increase the solubility of the polyimide resin in alkali aqueous solution, and is suitable for using as an insulation film in electronic and photoelectric products. The present invention also relates to preparation and use of the above polyimide.

10 Claims, 4 Drawing Sheets

WATER SOLUBLE POLYIMIDE RESIN, ITS PREPARATION AND USE

FIELD OF THE INVENTION

The present invention relates to a water soluble polyimide resin and its preparation, in particular to a water soluble polyimide resin showing good solubility in an aqueous alkaline solution, and having excellent heat-resistance, flexibility and insulating properties when forming into a film; thus it can be widely applied in electronic industries.

BACKGROUND OF THE INVENTION

Polyimide has been widely used as an insulating film in electronic industries due to its flexibility, excellent insulation and heat resistance. With advancing technique in electronic industries, much more electronic elements use polyimide film as insulating film. Moreover, with acknowledge of environmental protection, many studies focus on improvement of properties of the polyimide.

In semiconductors industries, a circuit board is obtained by covering photo-resist film on a substrate, exposing the photo-resist to radiation through a mask having a desired pattern, developing and removing the exposed part or the unexposed part with an aqueous alkaline solution, then etching the substrate to obtain a circuit having a desired pattern. As to the photo-resist film, an aromatic polyimide has been widely used.

Such an aromatic polyimide such as photosensitive polyimide has been disclosed in U.S. Pat. No. 4,321,319 and U.S. Pat. No. 6,001,534. However, the developing for such aromatic polyimide should be done by using organic solvent so that it is unfriendly to environment and is harmful to operators' health.

Moreover, U.S. Pat. No. 5,668,248 disclosed a poly(amic acid) ester resin obtained by esterfying the carboxy group contained in the poly(amic acid) with a compound having no vinyl group. However, a film produced from the poly(amic acid) ester will result in film shrinkage in thickness direction when subjecting it to cyclization at an elevated temperature. Also, obtaining the starting monomer used in '248 patent requires a complex process and it is unfavorable to its production.

In view of environmental protection and the problems encountered in prior arts, there needs a polyimide resin which is water soluble and can be developed by using aqueous solution other than organic solvents.

SUMMARY OF THE INVENTION

Thus the present invention provides a water soluble polyimide resin, which comprises a repeat unit (I) and a repeat unit (II) in a block or random arrangement:

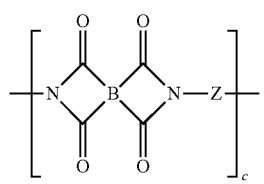
(I)

wherein B represents a tetravalent organic group; c represent a mole fraction for the repeating unit and is in the range of from 3 to 50 mole %, preferably from 5 to 30 mole %; and Z represent a group of the following formula:

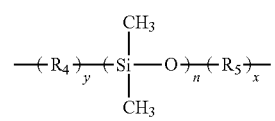

wherein $R_4$ and $R_5$ are the same or different, and each represents a alkylene group containing 1 to 6 carbon atoms, arylene group containing 6 to 20 carbon atoms, aralkylene containing 6 to 20 carbon atoms, or arylene-oxy-alkylene group containing 6 to 20 carbon atoms; n, x, and y each represents an integral equal to or more than 1;

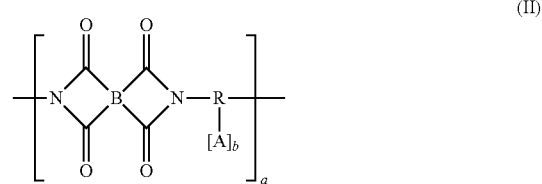
(II)

wherein B represents a tetravalent organic group; R represents a phenylene group; b represents a number of 0, 1, or 2; A represents a group selected from —OH and —COOH, when b is the number of 2, the plural A's are each the same or different; and a represents a mole fraction for the repeating unit and is in the range of from 50 to 97 mole %, preferably from 70 to 95 mole %.

The water soluble polyimide resin according to the present invention has a number average molecular weight ranging from 10,000 to 300,000, preferably from 40,000 to 100,000, as determined by Gel Permeation Chromatography (GPC) and converted into polystyrene; and has an inherent viscosity (IV) ranging from 0.20 to 0.95 dL/g, preferably from 0.20 to 0.40 dL/g.

In the present invention, the intrinsic viscosity is determined by the following steps: preparing a polymer solution containing a polymer in a concentration of 0.5 g/dL by using N-methylpyridone (NMP) as a solvent, measuring the viscosity of the solution by Ubbelohode viscometer after maintaining the polymer solution in water bath at 25° C. for 30 mins, and then calculating the inherent viscosity $\eta_{inh}$ according to the following equation:

$$\eta_{inh} = \ln(t/t0)/0.5 (g/dl)$$

wherein t0=time (in term of seconds) to pass two scale labels preset at upper and lower positions for the solvent (a blank);

t=time (in term of seconds) to pass two scale labels preset at upper and lower positions for the polymer solution.

The water soluble polyimide resin of the present invention has an excellent solubility in an aqueous alkaline solution. When the water soluble polyimide resin is coated into a film having a thickness of 10~25 μm, the resultant film (size: 9×5.5 cm) can be dissolved in 1000 mL 1 wt % sodium carbonate aqueous solution less than 130 seconds, i.e., it shows an excellent solubility in an aqueous alkaline solution.

In the present invention, the water soluble polyimide resin can be further reacted with a compound having a photosensitive group to form a water soluble photosensitive polyimide resin. For examples, when the present water soluble polyimide resin contains a hydroxyl group, i.e., A represents a hydroxyl group, it can further react with anhydride having a carbon-carbon double bond to obtain a polyimide resin having photosensitive group (i.e. ethylenic group). Examples of the anhydride include, but are not limited to, maleic anhydride, substituted maleic anhydride, tetrahydrophthalic anhydride, substituted tetrahydrophthalic anhydride, endomethylene tetrahydrophthalic anhydride, substituted endomethylene tetrahydrophthalic anhydride and the like.

The present invention also relates to a method for preparing the present water soluble polyimide resin as mentioned above, which comprises the following steps:

(a) reacting tetracarboxylic dianhydride, diamine having siloxane group, and diamine having a carboxyl and/or a hydroxyl group, to obtain a polyamic acid precursor having a carboxyl and/or a hydroxyl group; wherein the molar equivalent ratio of tetracarboxylic dianhydride to diamines is from 1:0.8 to 1:1.2, and the molar ratio of the diamine having siloxane group to the diamine having a carboxyl and/or a hydroxyl group is from 3:97 to 50:50, preferably from 5:95 to 30:70;

(b) heating the polyamic acid precursor having a carboxyl and/or a hydroxyl group obtained in the step (a) to obtain the polyimide comprising the repeat unit (I) and the repeat unit (II).

In the present method, to avoid the carboxy group contained in the diamine having hydroxyl and/or carboxy group reacts with the amino group contained in the diamine, it is preferable that the diamine having siloxane group first reacts with the tetracarboxylic dianhydride in excess amount of the tetracarboxylic dianhydride, and then reacts with the diamine having hydroxyl and/or carboxy group.

The present polyimide resin is useful as a photo-resist. Also, when it is used as a photo-resist and coated on a substrate such as copper foil to form a film, the thickness of the film would not reduce after it is exposed to irradiation and post-exposure bake.

The present invention also relates to a novel compound of 3,5-diamino-4-hydroxybenzoic acid, which is useful as an intermediate for preparing the polyimide resin of the present invention.

The present invention also relates to a novel compound of 3,5-diaminosalicylic acid (alternatively referred to 2-hydroxy-3,5-diaminobenzoic acid), which is useful as an intermediate for preparing the polyimide resin of the present invention.

The present invention also relates to a water-soluble polyimide resin composition, which comprises (A) the water soluble polyimide resin as mentioned above; (B) (meth) acrylic acid monomer as a diluent; and (C) photo-initiator, wherein the weight ratio of the component (A): the component (B) is 100:10~200, preferably 100:60~150; the component (C) is present in amount of from 0.1~15.0% by weight, preferably 1.0~10.0% by weight based on the weight of the component (A).

DETAILED DESCRIPTION OF THE INVENTION

Figure 1:
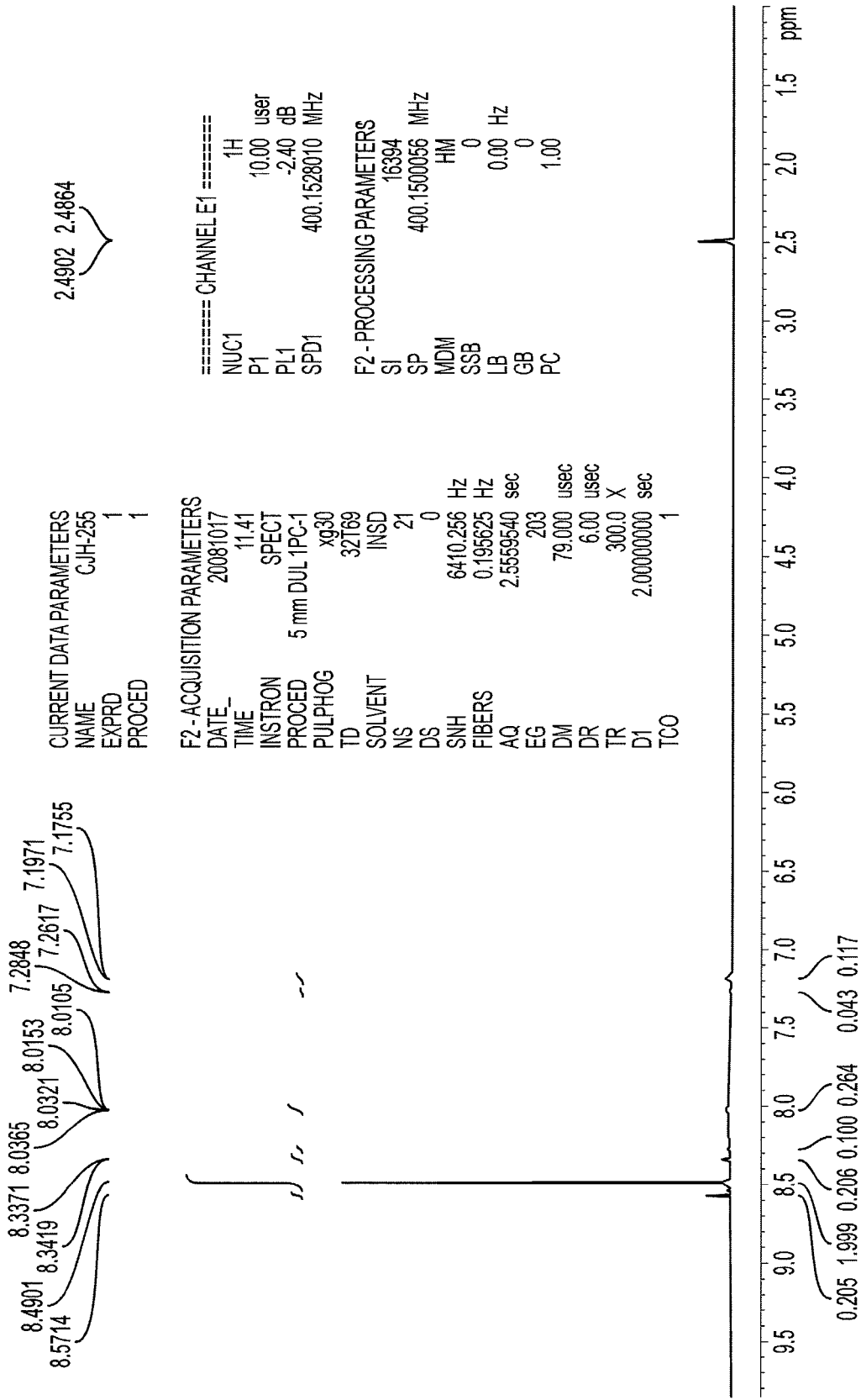
FIG. 1 shows an NMR spectrum for the compound prepared in Production Example 1.

Examples of the tetracarboxylic dianhydride used for preparing the present polyimide resin include, but are not limited to, 2,2'-di(3,4-di-carboxylphenyl)hexafluoropropane dianhydride (6FDA), pyromellitic dianhydride(PMDA), 4,4'-oxydiphthalic anhydride(ODPA), 3,3',4,4'-biphenyltetracarboxylic dianhydride(BPDA), 3,3',4,4'-benzophenonetetracarboxylic dianhydride (BTDA), ethylene tetracarboxylic dianhydride, butane tetracarboxylic dianhydride, cyclopentanetetracarboxylic dianhydride, 2,2',3,3'-benzophenone-tetracarboxylic dianhydride, 2,2',3,3'-biphenyl-tetracarboxylic dianhydride, 2,2-di(3,4-dicarboxylphenyl)propane dianhydride, 2,2-di(2,3-dicarboxylphenyl)propane dianhydride, di(3,4-dicarboxylphenyl)ether dianhydride, di(3,4-dicarboxylphenyl)sulfone dianhydride, 1,1-di(2,3-dicarboxylphenyl)ethane dianhydride, di(2,3-dicarboxyl-phenyl)methane dianhydride, di(3, 4-dicarboxylphenyl)methane dianhydride, 4,4'-(p-phenylenedioxy)diphthalic dianhydride, 4,4'-(m-phenylenedioxy)diphthalic dianhydride, 2,3,6,7-naphthalene-tetracarboxylic dianhydride, 1,4,5,8-naphthalenetetracarboxylic dianhydride, 1,2,5,6-naphthalenetetracarboxylic dianhydride, 1,2,3,4-benzenetetracarboxylic dianhydride, 3,4,9,10-perylenetetracarboxylic acid dianhydride, 2,3,6,7-anthracene-tetracarboxylic dianhydride and 1,2,7,8-phenanthrene-tetracarboxylic dianhydride, etc. These dianhydride can be used alone or as a mixture of more species.

Examples of the diamine having carboxy and/or hydroxyl group used for preparing the present polyimide resin include, but are not limited to, 3,5-diamino-4-hydroxy-benzoic acid (DAPHBA), 3,5-diaminosalicylic acid (DASA, or termed as 2-hydroxy-3,5-diaminobenzoic acid), and 3,5-diaminobenzoic acid (DABZ) and the like.

Examples of the diamine having siloxane group used for preparing the present polyimide resin include, but are not limited to, 1,3-di(3-aminopropyl)-1,1,3,3-tetramethyl-disiloxane(DSI), 1,3-di(4-aminobutyl)-1,1,3,3-tetramethyldisiloxane, 1,3-di(3-aminopropyl)-1,3-dimethyl-1,3-diphenyldisiloxane, 1,3-di(3-aminophenyl)-1,1,3,3-tetramethyldisiloxane, 1,3-di(4-aminophenyl)-1,1,3,3-tetramethyldisiloxane, 1,3-di(3-aminophenoxymethyl)-1,1,3,3-tetramethyldisiloxane, 1,3-di(4-aminophenoxymethyl)-1,1, 3,3-tetra-methyldisiloxane, polysiloxane diamine (MW=900) etc.

In the present method for preparing polyimide, in addition to the above-mentioned diamine having a siloxane group and diamine having a hydroxyl and/or carboxy group, the polyimide can contain other repeating units derived from other diamine as long as it would not adversely affect the desired effect of the present polyimide resin. Examples of the other diamine include, but are not limited to, p-phenylene diamine (PDA), 4,4'-oxydianiline(ODA), 1,3-di(4-aminophenoxy)-benzene(TPE-R), 2,2-bi[4-(4-aminophenoxy)phenyl]propane(BAPP), bi[4-(4-amino-phenoxy)phenyl]sulfone (BAPS), 1,3-di(3-aminophenoxy)benzene(APB), 4,4'-bi(4-aminophenoxy)-3,3'-dihydroxybiphenyl(BAPB), di[4-(3-aminophenoxy)phenyl]methane, 1,1-di[4-(3-aminophenoxy)phenyl]-ethane, 1,2-di[4-(3-amino-phenoxy) phenyl]ethane, 2,2-di[4-(3-amino-phenoxy)phenyl]propane, 2,2'-di[4-(3-aminophenoxy)phenyl]butane, 2,2-di[4-(3-amino-phenoxy)phenyl]-1,1,1,3,3,3-hexafluoropropane, 4,4'-di(3-aminophenoxy)biphenyl, di[4-(3-aminophenoxy) phenyl]ketone, di[4-(3-amino-phenoxy)phenyl]sulfide, di[4-(3-aminophenoxy)phenyl]-sulfoxide, di[4-(3-aminophenoxy)phenyl]sulfone, di[4-(3-amino-phenoxy)phenyl]ether etc. The above diamines can be used individually or as a mixture of more species.

In case of using the other diamines, the weight ratio of the other diamine to the total weight of the diamine having a carboxy and/or hydroxyl group and the diamine having a siloxane group is from 70:30 to 90:10. However, the ratio of total mole equivalent of the tetracarboxylic dianhydride to the diamine should range from 1:0.8 to 1:1.2.

In the present method, the reaction of tetracarboxylic dianhydride and diamine is carried out in an aprotic polar solvent, there is no special restriction on the aprotic polar solvent, as long as the solvent does not react with reactants or the product. Examples of the solvents are, for example, N,N-dimethylacetamide(DMAc), N-methylpyrrolidone(NMP), N,N-dimethylformamide(DMF), tetrahydrofuran(THF), dioxane, chloroform ($CHCl_3$), dichloromethane etc. Among them, N-methylpyrrolidone(NMP) and N,N-dimethylacetamide (DMAc) are preferable.

In the present method, the reaction of tetracarboxylic dianhydride and diamine is generally carried out at a temperature of from room temperature to 90° C., and preferably from 30 to 75° C.

The present invention also relates to a water-soluble polyimide resin composition, which comprises (A) the water soluble polyimide resin defined as above; (B) (meth)acrylic acid monomer as a diluent; and (C) photo-initiator, wherein the weight ratio of the component (A): the component (B) is 100:10~200; the component (C) is present in amount of from 0.1~15.0% by weight based on the weight of the component (A).

In the present water-soluble polyimide resin composition, the component (B) serves as a diluent. Furthermore, since component (B) contains vinyl functional group in the molecular, it also facilitates the curing reaction for the composition when exposing to radiation. Examples of the component (B) include, but are not limited to, ethylene glycol diacrylate, propylene glycol diacrylate, butylene glycol diacrylate, diethylene glycol diacrylate, dipropylene glycol diacrylate, trimethylolpropane triacrylate, triethylolpropane triacrylate, pentaerythritol diacrylate, dipentaerythritol triacrylate, ethylene glycol dimethacrylate, propylene glycol dimethacrylate, butylene glycol dimethacrylate, diethylene glycol dimethacrylate, dipropylene glycol dimethacrylate, trimethylolpropane trimethacrylate, triethylolpropane trimethacrylate, pentaerythritol dimethacrylate, and dipentaerythritol trimethacrylate etc.

When the polyimide resin of the present invention is formulated as a photoresist, a photoinitiator can be incorporated, i.e., the component (C) used in the resin composition. The photoinitiator used in formulating the composition is a compound which molecular structure will decompose into free radicals, cation or anion active sites upon exposure of visible light, ultra-violet light, far ultra-violet light, electron beam and X-ray, and induce the polymerization of the polyimide and the (meth)acrylate monomer.

Examples of the photoinitiators include, but are not limited to, imidazoles such as 2,2'-di(2-chlorophenyl)-4,4',5,5'-tetra(4-ethoxy-carbonylphenyl)-1,2'-di-imidazole, 2,2'-di(2-bromophenyl)-4,4',5,5'-tetra(4-ethoxycarbonylphenyl)-1,2'-di-imidazole, 2,2'-di(2,4-dichloro-phenyl)-4,4',5,5'-tetraphenyl-1,2'-di-imidazole, 2,2'-di(2,4,6-trichloro-phenyl)-4,4',5,5'-tetraphenyl-1,2'-di-imidazole, 2,2'-di(2,4-dibromo-phenyl)-4,4',5,5'-tetraphenyl-1,2'-di-imidazole, and 2,2'-di(2,4,6-tribromophenyl)-4,4',5,5'-tetraphenyl-1,2'-di-imidazole;

phosphine oxides such as triphenylphosphine oxide(TPO, commercial available from BASF), di(2,4,6-trimethyl-benzoyl)phenylphosphine oxide [Irgacure 819, (IR819), commercial available from Ciba Geigy Corporation]; alkylphenyl ketones such as 1-hydroxycyclohexylphenyl ketone [Irgacure 184(IR184), commercial available from Ciba Geigy Corporation], 2-methyl-(4-methylthienyl)-2-morpholinyl-1-propan-1-one [Irgacure 907(IR907), commercial available from Ciba Geigy Corporation] etc.;

benzoins photoinitiator, such as benzoin, benzoin methyl ether, benzoin ethyl ether, benzoin isopropyl ether, benzoin isobutyl ether, methyl-2-benzoylbenzoate, etc., and similar derivatives thereof;

acetophenones, such as 2,2-dimethoxy-2-phenylacetophenone [Irgacure 651(IR651), commercial available from Ciba Geigy Corporation], 2-hydroxy-2-methyl-1-phenylpropan-1-one, 1-(4-isopropyl-phenyl)-2-hydroxy-2-methylpropan-1-one, 4-(2-hydroxyethoxy)phenyl-(2-hydroxy-2-propyl)ketone, 2,2-dimethoxyacetophenone, 2,2-diethoxyacetophenone, 2-benzyl-2-dimethylamino-1-(4-morpholinylphenyl)-butan-1-one, 2,2'-dimethoxy-1,2-diphenylethan-1-one, 4-azido-acetophenone, 4-azido-benzylidene acetophenone, etc., and similar derivatives thereof;

benzophenones, such as benzophenone, 4,4'-di(dimethylamino)-benzophenone, 4,4'-di(diethylamino)-benzophenone, 3,3'-dimethyl-4-methoxy benzophenone, and similar derivatives thereof;

a photoinitiator having an a-diketone structure such as diacetoformate, dibenzoylformate, methylbenzoylformate, etc., and similar derivatives thereof; a photoinitiator having a multinuclear quinone structure such as anthraquinone, 2-ethylanthraquinone, 2-tertbutyl-anthraquinone, 1,4-naphthoquinone, etc., and similar derivatives thereof; a photoinitiator having a xanthone structure such as xanthone, thioxanthone, 2,4-diethylthioxanthone, 2-chlorothioxanthone, etc., and similar derivatives thereof; a photoinitiator having a diazo structure such as 4-diazodiphenylamine, 4-diazo-4'-methoxy-diphenylamine, 4-diazo-3-methoxydiphenyl-amine etc. and similar derivatives thereof; a photoinitiator with a triazine structure such as 2-(2'-furanyl-ethylidene)-4,6-di(trichloromethyl)-s-triazine, 2-(3',4'-dimethoxy-styryl)-4,6-di-(trichloromethyl)-s-triazine, 2-(4'-methoxynaphthyl)-4,6-di-(trichloromethyl)-s-triazine, 2-(2'-bromo-4'-methylphenyl)-4,6-di-(trichloromethyl)-s-triazine, 2-(2'-thienylethylidene)-4,6-di(trichloro-methyl)-s-triazine etc., and similar derivatives thereof.

These photoinitiators can be used alone or in a mixture of more than 2 species. The content of the photoinitiator is from 0.1~15.0 weight %, preferably 1.0~5.0 weight %, based on the weight of component (A).

EXAMPLES

The present invention will be described in detail below with reference to Production Examples, Examples & Formulation Examples for purposes of exemplification and illustration only and not to limit the scope of the present invention.

In the following Production Examples, Examples & Formulation Examples, abbreviation are as follows.
6-FDA: 2,2'-di(3,4-dicarboxyphenyl)hexafluoropropane dianhydride (Mw=444)
BTDA: 3,3',4,4'-benzophenone tetracarboxylic dianhydride (MW=322.2)
DAPHBA: 3,5-diamino-4-hydroxy-benzoic acid (Mw=168.15)
DABZ: 3,5-diaminobenzoic acid (Mw=152.25)
HA6F: 2,2-di(3-hydroxy-4-aminophenyl)-1,1,1,3,3,3-hexafluoropropane (Mw=366.3)
ODA: 4,4'-oxydianiline (Mw=200.2)
PSLX: polysiloxane diamine (Mw=900)

NMP: N-methyl-2-pyrrolidine
Catalyst: M/carbon, M/alumina, in which M=Pt, Pd, Rh, Ru, Ni and other transition metals and the carbon and alumina are both supporter.
Preparation of Starting Monomer:

Production Example 1

Preparation of 3,5-dinitro-4-hydroxybenzoic acid (DNPHBA)

In a 3-liter reactor, 138 g p-hydroxybenzoic acid (PHBA, Mw=168, manufactured and sold by Chang Chun Plastics Co., Ltd.) was immersed in 588 g of 98% conc. sulfuric acid with stirring slowly to avoid agglomeration. The reactor was placed in a ice-water bath and 190 g of 98% conc. nitric acid was added drops into the above solution over 1.5 hours by using addition funnel with controlling addition rate under maintaining the reaction temperature at 20~40° C. while stirring. While maintaining in ice-water bath, 1.5 L iced water was quickly added into the resultant solution to quench the nitration. During the addition, it should be careful due to the exothermic reaction. After continuously stirring for 15 minutes, the solid was filtered and washed by 500 mL pure water to obtain solid 3,5-diamino-4-hydroxybenzoic acid (DNPHBA) in yellow color. Yield: 91.7% (m.p.: 237° C., DSC).

Figure 2:
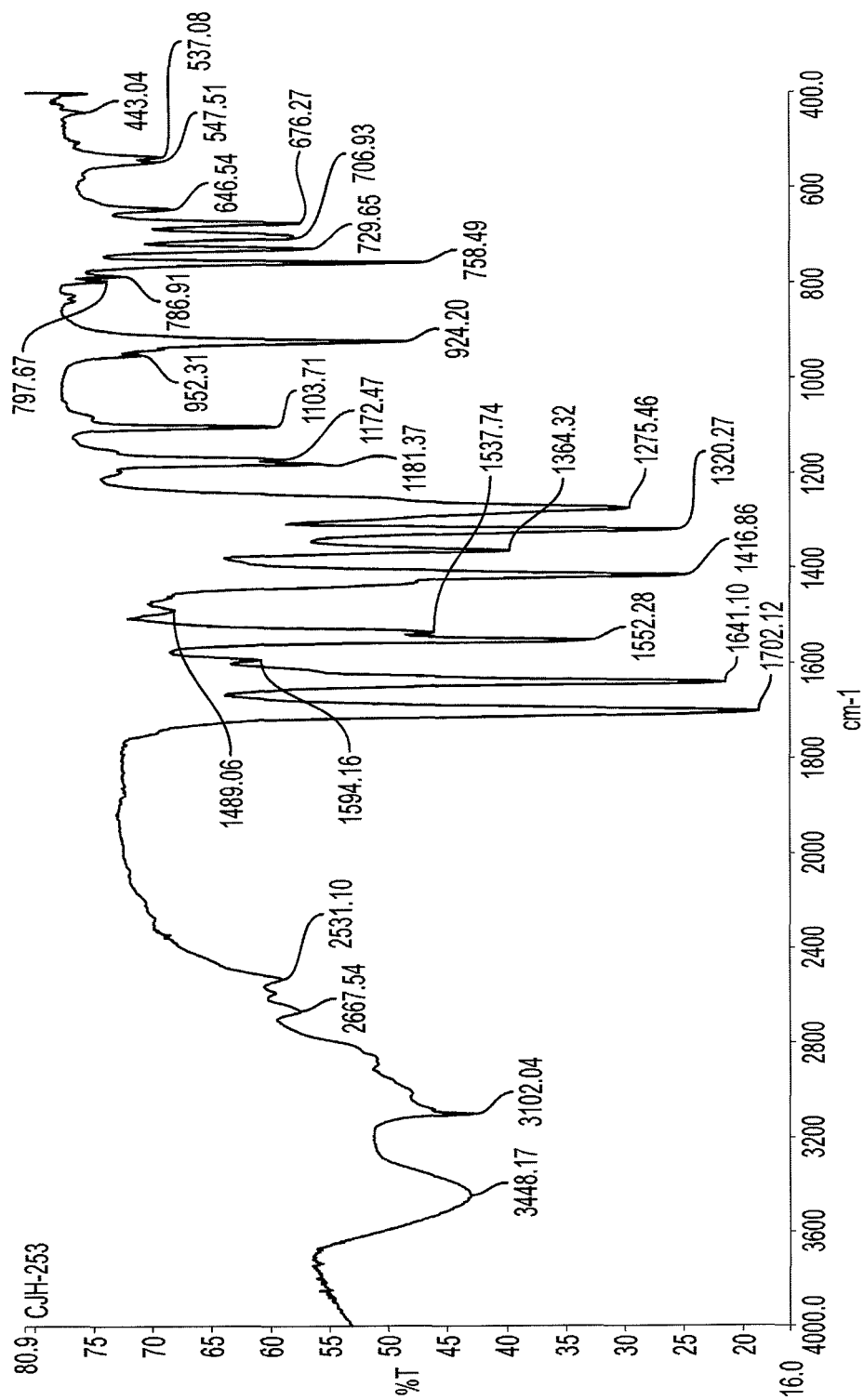
FIG. 2 shows an IR spectrum for the compound prepared in Production Example 1.

The $^1$H-NMR spectrum and IR spectrum for the compound are shown in FIGS. 1 and 2, respectively. In the $^1$H-NMR spectrum, the proton on benzene ring will be shifted to about 8.5 ppm due to the electron withdrawing property attributed to $NO_2$ and COOH groups. In the IR spectrum, it was found a peak for OH at 3348 $cm^{-1}$, a peak for COOH at 1702 $cm^{-1}$ and peaks for nitro group at 1552 and 1320 $cm^{-1}$.

Production Example 2

Preparation of 3,5-diamino-4-hydroxybenzoic acid (DAPHBA)

In an autoclave, 40 g of the crude DNPHBA produced in the above Production Example 1 was dissolved in 1200 mL methanol. After dissolving completely, the solution was degassed by purging nitrogen for 10 minutes, and slowly added with 38 g of 98% conc. sulfuric acid and then added with 1 g of catalyst Pd/C. The autoclave was sealed and bubbled with hydrogen at a pressure of 7 kg/$cm^2$ for further reacting about 12 to 16 hours. After hydrogen was no longer consumed, the pressure in the autoclave was released to normal pressure and the suspended solid in the autoclave was taken out and filtered. The resultant solid was added into 188 g of 4N hydrochloric acid solution under nitrogen atmosphere and 2 g of $SnCl_2.H_2O$ was added and then heated at 90° C. to allow solid dissolving completely. The resultant solution was hot filtered to filter the hydrogenation catalyst off. The filtered solution was cooled down to solidify 22 g of product 3,5-diamino-4-hydroxybenzoic acid (DNPHBA). The product was placed on a iron tray and found some erosion on the tray. Thus it concluded that the product is hydrochloride salt, which can be used for preparing the present water soluble polyimide.

Production Example 3

Alternative Preparation of 3,5-diamino-4-hydroxybenzoic acid (DAPHBA)

In an autoclave, 20 g of the crude DNPHBA produced in the above Production Example 1 was dissolved in 100 mL tetrahydrofuran and 50 mL methanol. After dissolving completely, the solution was degassed by purging nitrogen for 10 minutes, and slowly added with 19.5 g of 98% conc. sulfuric acid and then added with 250 mg of catalyst Pd/C. The autoclave was sealed and bubbled with hydrogen at a pressure of 7 kg/$cm^2$ for further reacting about 12 to 16 hours. After hydrogen was no longer consumed, the pressure in the autoclave was released to normal pressure and the suspended solid in the autoclave was taken out and filtered. The resultant solid was mixed with 493 g of pure water and heated at 85° C. to allow solid dissolving completely. The resultant solution was hot filtered to filter the hydrogenation catalyst off. The filtered solution was distilled under reduced pressure with recovery pure water until all solids were solidified. The solid was added with 400 mL iso-propanol to subject to recrytalization to obtain 15.8 g of product 3,5-diamino-4-hydroxybenzoic acid (DNPHBA), m.p.=248.6° C.

Figure 3:
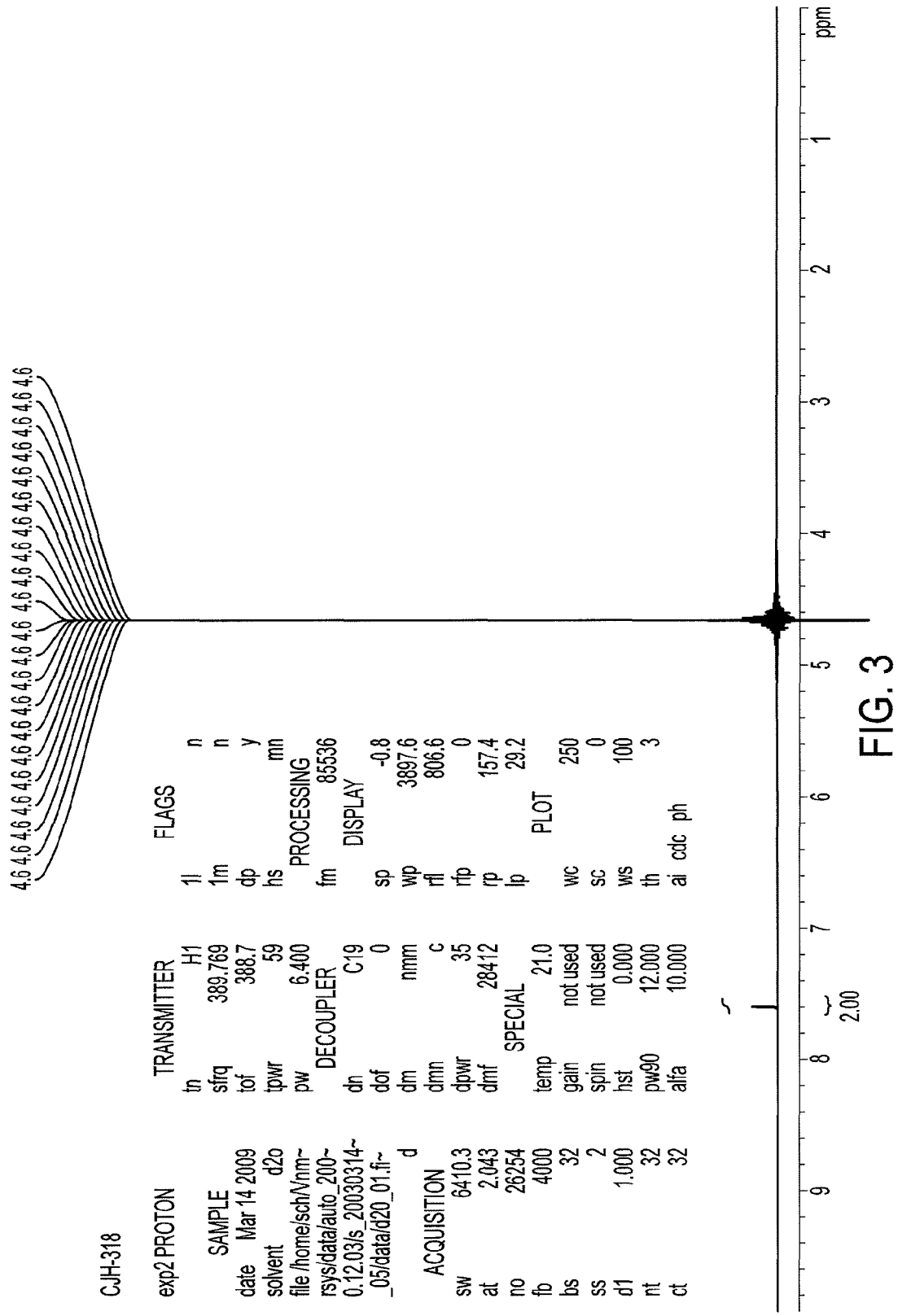
FIG. 3 shows an NMR spectrum for the compound prepared in Production. Example 3.
Figure 4:
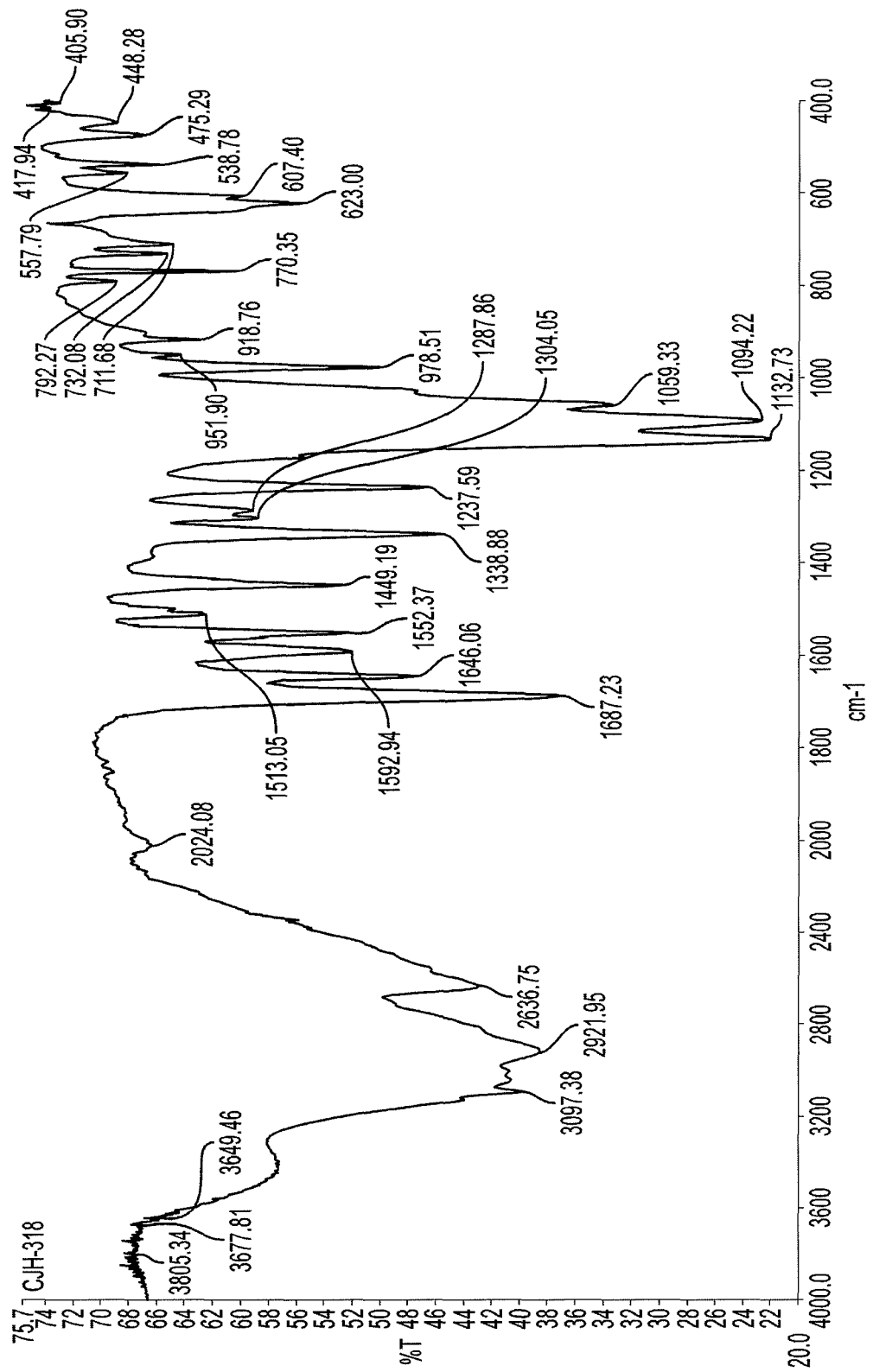
FIG. 4 shows an IR spectrum for the compound prepared in Production Example 3.

The $^1$H-NMR spectrum and IR spectrum for the compound are shown in FIGS. 3 and 4, respectively. In the $^1$H-NMR spectrum, the proton on benzene ring will be shifted to about 7.6 ppm since the electron withdrawing group $NO_2$ was reduced to electron donating group $NH_2$, and the other protons were obscured with the solvent $D_2O$ used in the NMR analysis. In the IR spectrum, it was found a peak for NH and OH at 3500~2600 $cm^{-1}$, a peak for COOH at 1687 $cm^{-1}$ and peaks for C—N stretching at 1162~1000 $cm^{-1}$.

Production Example 4

Preparation of 3,5-dinitrosalicylic acid (DNSA)

In a 3-liter reactor, 138 g salicylic acid was immersed in 588 g of 98% conc. sulfuric acid with stirring slowly to avoid agglomeration. The reactor was placed in a ice-water bath and 190 g of 98% conc. nitric acid was added drops into the above solution over 1.5 hours by using addition funnel with controlling addition rate under maintaining the reaction temperature at 20~40° C. while stirring. While maintaining in ice-water bath, 1.5 L iced water was quickly added into the resultant solution to quench the nitration. During the addition, it should be careful due to the exothermic reaction. After continuously stirring for 15 minutes, the solid was filtered and washed by 500 mL pure water to obtain solid 3,5-dinitrosalicylic acid (NNSA) in yellow color. Yield: 84% (m.p.: 167.7° C., DSC).

Production Example 5

Preparation of 3,5-diaminosalicylic acid (DASA)

In an autoclave, 20 g of the crude DNSA produced in the above Production Example 4 was dissolved in 150 mL methanol. The solution was degassed by purging nitrogen for 10 minutes, and slowly added with 19.5 g of 98% conc. sulfuric acid and then added with 250 mg of catalyst Pd/C. The autoclave was sealed and bubbled with hydrogen at a pressure of 7 kg/$cm^2$ for further reacting about 12 to 16 hours. After hydrogen was no longer consumed, the pressure in the autoclave was released to normal pressure and the suspended solid in the autoclave was taken out and filtered. The resultant solid was mixed with 600 g of pure water and heated at 85° C. to allow solid dissolving completely. The resultant solution was hot filtered to filter the hydrogenation catalyst off. The filtered solution was distilled under reduced pressure with recovery pure water until all solids were solidified. The solid was added with 450 mL iso-propanol to subject to recrytalization to obtain 17.3 g of product 3,5-diaminoalicylic acid (DASA), m.p.=246.7° C.

Production of Polyimide

Example 1

Into a 500 mL glass reactor, 44.4 g of 2,2-di(3,4-benaene dicarboxylic anhydride) perfluoropropane (6FDA, Mw=444, 0.1 mole) and 250 g of N-metyhylpyrrolidone (NMP) were added and stirred at room temperature until dissolving. 27.0 g of polysiloxane diamine (PSLX, Mw=900, 0.03 mole) were added drop into the reactor and maintained the inner temperature of the reactor not exceeding 35° C. and further stirred for 2 hours. Then 11.43 g of NAPHBA (0.068 mole) produced in the above Production Example 3 were slowly added into the reactor and continuously stirred for 12 hours at room temperature. And then 30 g of toluene were added into the reactor and reaction temperature was increased to 150° C. for further reflux reacting for 8 hours to obtain water soluble polyimide solution, which was referred to PI-1. The inherent viscosity (IV) of PI-1 was determined as 0.23 dL/g and its number average molecular weight (Mn) was 61000. The scheme for the above reaction is a follows.

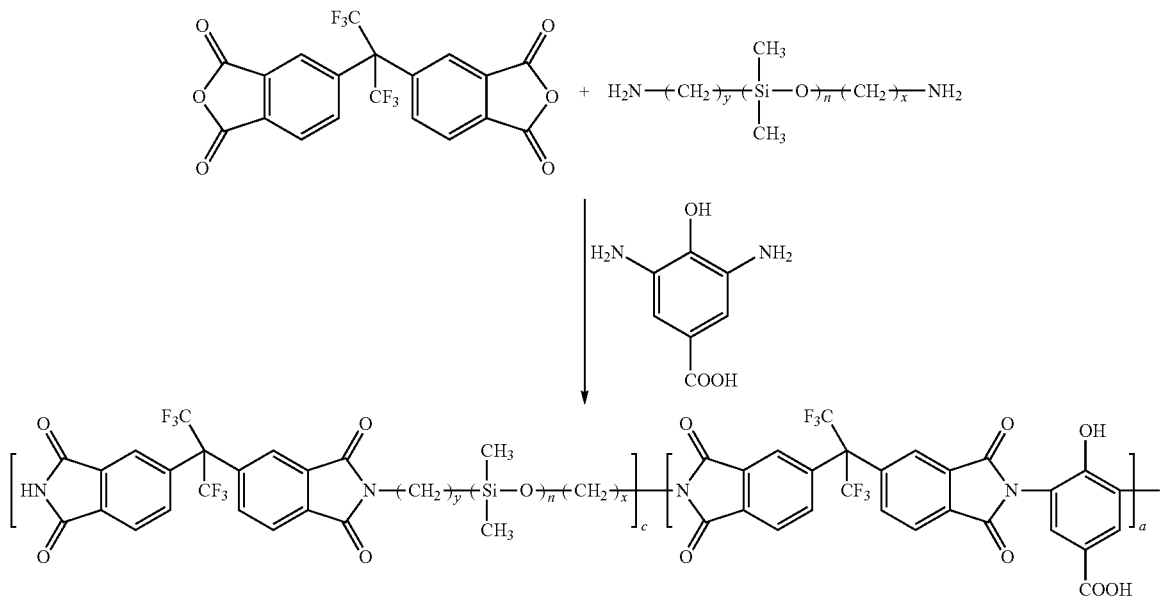

wherein a represents a mole fraction for NAPHBA and c represents a mole fraction for PSLX.

Example 2

Into a 500 mL glass reactor, 44.4 g (0.1 mole) of 6FDA and 251 g of NMP were added and stirred at room temperature until dissolving. 27.0 g (0.03 mole) of PSLX were added drop into the reactor and maintained the inner temperature of the reactor not exceeding 35° C. and further stirred for 2 hours. Then 8.4 g (0.05 mole) of NAPHBA produced in the above Production Example 3 and 2.74 g of 3,5-diaminobenzoic acid (DABZ, Mw=152.25, 0.018 mole) were slowly added into the reactor and continuously stirred for 12 hours at room temperature. And then 30 g of toluene were added into the reactor and reaction temperature was increased to 150° C. for further reflux reacting for 8 hours to obtain water soluble polyimide solution, which was referred to PI-2. The inherent viscosity (IV) of PI-2 was 0.24 dL/g and number average molecular weight (Mn) was 62500.

Example 3

Into a 500 mL glass reactor, 44.4 g (0.1 mole) of 6FDA and 250 g of NMP were added and stirred at room temperature until dissolving. 9.0 g (0.01 mole) of PSLX were added drop into the reactor and maintained the inner temperature of the reactor not exceeding 35° C. and further stirred for 2 hours. Then 14.8 g (0.088 mole) of NAPHBA produced in the above Production Example 3 were slowly added into the reactor and continuously stirred for 12 hours at room temperature. And then 30 g of toluene were added into the reactor and reaction temperature was increased to 150° C. for further reflux reacting for 8 hours to obtain water soluble polyimide solution, which was referred to PI-3. The inherent viscosity (IV) of PI-3 was 0.35 dL/g and number average molecular weight (Mn) was 83600.

Example 4

Into a 500 mL glass reactor, 32.2 g of 3,3',4,4'-benzophenone-tetracarboxylic dianhydride (BTDA, Mw=322.2, 0.1 mole) and 215 g of NMP were added and stirred at room temperature until dissolving. 27.0 g (0.03 mole) of PSLX were added drop into the reactor and maintained the inner temperature of the reactor not exceeding 35° C. and further stirred for 3 hours. Then 6.73 g (0.04 mole) of NAPHBA produced in the above Production Example 3 and 5.6 g of 4,4'-oxydianiline (ODA, Mw=200.2, 0.028 mole) were slowly added into the reactor and continuously stirred for 12 hours at room temperature. And then 26 g of toluene were added into the reactor and reaction temperature was increased to 150° C. for further reflux reacting for 8 hours to obtain water soluble polyimide solution, which was referred to PI-4. The inherent viscosity (IV) of PI-4 was 0.21 dL/g and number average molecular weight (Mn) was 59500.

Example 5

Into a 500 mL glass reactor, 32.2 g (0.1 mole) of BTDA and 215 g of NMP were added and stirred at room temperature until dissolving. 27.0 g (0.03 mole) of PSLX were added drop into the reactor and maintained the inner temperature of the reactor not exceeding 35° C. and further stirred for 3 hours. Then 1.68 g (0.01 mole) of NAPHBA produced in the above Production Example 3, 3.045 g of 3,5-diaminobenzoic acid (DABZ, 0.02 mole) and 7.61 g (0.038 mole) of ODA were slowly added into the reactor and continuously stirred for 15 hours at room temperature. And then 30 g of toluene were added into the reactor and reaction temperature was increased to 150° C. for further reflux reacting for 8 hours to obtain water soluble polyimide solution, which was referred to PI-5. The inherent viscosity (IV) of PI-5 was 0.20 dL/g and number average molecular weight (Mn) was 59000.

Example 6

Into a 500 mL glass reactor, 44.4 g (0.1 mole) of 6FDA and 250 g of NMP were added and stirred at room temperature until dissolving. 27.0 g (0.03 mole) of PSLX were added drop into the reactor and maintained the inner temperature of the reactor not exceeding. 35° C. and further stirred for 2 hours. Then 11.43 g (0.068 mole) of DASA produced in the above Production Example 5 were slowly added into the reactor and continuously stirred for 12 hours at room temperature. And then 30 g of toluene were added into the reactor and reaction temperature was increased to 150° C. for further reflux reacting for 8 hours to obtain water soluble polyimide solution, which was referred to PI-6. The inherent viscosity (IV) of PI-6 was 0.18 dL/g and number average molecular weight (Mn) was 48300.

Comparative Example 1

Into a 500 mL glass reactor, 44.4 g (0.1 mole) of 6FDA and 290 g of NMP were added and stirred at room temperature until dissolving. 27.0 g (0.03 mole) of PSLX were added drop into the reactor and maintained the inner temperature of the reactor not exceeding 35° C. and further stirred for 2 hours. Then 24.9 g of 2,2-bis(3-hydroxy-4-aminophenyl)-1,1,1,3,3, 3-heaxfluoropropane (HA6F, Mw=366.3, 0.068 mole) were slowly added into the reactor and continuously stirred for 12 hours at room temperature. And then 35 g of toluene were added into the reactor and reaction temperature was increased to 150° C. for further reflux reacting for 8 hours to obtain water soluble polyimide solution, which was referred to PI*-1. The inherent viscosity (IV) of PI*-1 was 0.18 dL/g and number average molecular weight (Mn) was 57600.

Comparative Example 2

Into a 500 mL glass reactor, 32.2 g (0.1 mole) of BTDA and 215 g of NMP were added and stirred at room temperature until dissolving. 27.0 g (0.03 mole) of PSLX were added drop into the reactor and maintained the inner temperature of the reactor not exceeding 35° C. and further stirred for 3 hours. Then 10.99 g (0.03 mole) of HA6F and 7.6 g (0.038 mole) of ODA were slowly added into the reactor and continuously stirred for 15 hours at room temperature. And then 30 g of toluene were added into the reactor and reaction temperature was increased to 150° C. for further reflux reacting for 8 hours to obtain water soluble polyimide solution, which was referred to PI*-2. The inherent viscosity (IV) of PI*-2 was 0.21 dL/g and number average molecular weight (Mn) was 59800.

Formulation of Negative Photo-Sensitive Polyimide Resin Composition Formulation Examples 1 to 3

100 g of each PI-1, PI-2, and PI-3 resin was well mixed with 20 g of tetraethylene glycol dimethacrylate, 2 g of benzophenone, 0.05 g of Michler's ketone, and 1 g of N-phenyl-diethanolamine, and 1.5 g of 2-mercapto-benzoimidazole to obtain negative photo-sensitive polyimide resin composition, respectively, which were each referred to VA-1 to VA-3.

Comparative Formulation Example 1

100 g of each PI*-1 resin was well mixed with 20 g of tetraethylene glycol dimethacrylate, 2 g of benzophenone, 0.05 g of Michler's ketone, and 1 g of N-phenyl-diethanolamine, and 1.5 g of 2-mercapto-benzoimidazole to obtain negative photo-sensitive polyimide resin composition which was referred to VA*-1.

Formulation of Positive Photo-Sensitive Polyimide Resin Composition Formulation Examples 4 and 5

100 g of each PI-4 and PI-5 resin was well mixed with 12 g of dimethoxy-anthrancene-sulfonic acid diphenyl-imidazole to obtain positive photo-sensitive polyimide resin composition, respectively, which were each referred to VA-4 to VA-5.

Comparative Formulation Example 2

100 g of PI*-2 resin was well mixed with 12 g of dimethoxy-anthrancene-sulfonic acid diphenyl-imidazole to obtain positive photo-sensitive polyimide resin composition, which were referred to VA*-2.

Preparation of Dry Film of Photo-Sensitive Polyimide and Determination of Physical Properties The prepared polyimide resin composition were each coated on a polyethylene terephthalate (PET) substrate by using a doctor coater (gap=100 μm) and baked on a hot plate at a temperature of 90° C. for 20 minutes to form a polyimide film. The baked polyimide film was each laminated on a copper foil (CCP-ED copper foil, produced by Chang Chun Plastics Co., Ltd., ⅓ ounce) at a temperature of 120° C. and a pressure of 1 khf/cm to obtain a laminate. The laminate was subjected to destruction test for corrosion as follows. The results were listed in Table 1.

Destruction Test for Corrosion (Also Referred to Solubility Test):

Polyimide resin was cast into a film having a thickness of 10~25 μm. From the film was cut off a specimen in size of 9*5.5 $cm^2$ and dissolved in 1000 mL of 1 wt % $Na_2CO_3$ aqueous solution and determined the time when the film was completely dissolving in the solution.

Resolution Test:

The polyimide film on the laminate was irradiated with UV light at 300 mJ/$cm^2$ through a mask having a desired pattern by using an ultraviolet exposure (manufactured by ORC Manufacturing Co.) and then developed with 1 wt % $Na_2CO_3$ aqueous solution and washed with pure water to form a photoresist pattern. The developed laminate was baked in an oven at 100° C. for 1 hour, at 150° C. for 1 hour, and at 200° C. for 1 hour. The pattern was determined whether the profile is well and determined the least width (sosolution) by using a magnifier and scanning electron microscope (SEM). The results are shown in Table 1.

Peeling Strength Test:

The film was peel from the copper foil by using Tensile Teat Machine(Model HT-9102, commercial available from Hung Ta Instrument Co., Ltd., Taiwan) to determine the applied force when the film separating from the copper foil. The results are shown in Table 1.

Solder Test:

The baked polyimide as above was cut off a specimen in size of 3×3 $cm^2$ and the specimen was immersed in molten solder bath at a temperature of 320° C. for 5 minutes and taken out for observing whether inflation between the film and the copper foil occurred. If no inflation occurred, it was judged as test "pass".

TABLE 1

| Polyimide film | Solubility (sec) | Profile of pattern | Resolution (μm) | Thickness of film (μm) | Peeling strength (kg/cm²) | Solder test (320° C./ 5 mins) |
|---|---|---|---|---|---|---|
| VA-1 | 110 | Good | 60 | 20 | 1.1 | Pass |
| VA-2 | 120 | Good | 60 | 19 | 1.0 | Pass |
| VA-3 | 90 | Good | 60 | 18 | 1.0 | Pass |
| VA-4 | 90 | Good | 50 | 20 | 1.2 | Pass |
| VA-5 | 100 | Good | 50 | 18 | 1.1 | Pass |
| VA*-1 | >300 | Not available | Not available | 20 | 1.1 | Pass |
| VA*-2 | >300 | Not available | Not available | 19 | 1.2 | Pass |

From Table 1, it is known that the polyimide resin prepared by polymerizing the present diamine having a —OH and/or —COOH functional group and dianhydride exhibits excellent solubility in aqueous alkali solution. Moreover, the polyimide films produced from the present polyimide resins exhibit physical properties comparable with those produced from VAS*-1 and VA*-2 but exhibits better solubility in alkali aqueous solution. Accordingly, the polyimide film produced from the present polyimide resin could be developed by using alkali aqueous solution without using organic solvent and thus it is benefit to the work environment and environmental protection. Additionally, since the present polyimide resin contains —OH and/or —COOH group, which could further react with other anhydrides to form three-dimension network structure and improve the physical properties of the resultant polyimide resin.

What is claimed is:

1. A water soluble polyimide resin, which consists of a repeat unit (I) and a repeat unit (II) in a block or random arrangement:

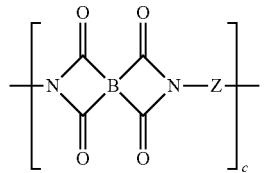

(I)

wherein B represents a tetravalent organic group; c represent a mole fraction for the repeating unit and is in the range of from 3 to 50 mole %; and Z represent a group of the following formula:

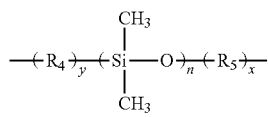

wherein $R_4$ and $R_5$ are the same or different, and each represents a alkylene group containing 1 to 6 carbon atoms, arylene group containing 6 to 20 carbon atoms, aralkylene containing 6 to 20 carbon atoms, or arylene-oxy-alkylene group containing 6 to 20 carbon atoms; n, x, and y each represents an integral more than or equal to 1;

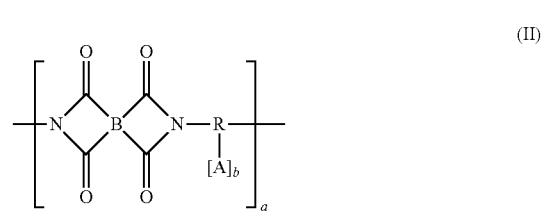

(II)

wherein B represents a tetravalent organic group; R represents a phenylene group; b represents a number of 1 or 2; A represents a group selected from —OH and —COOH, when b is the number of 2, the plural A's are each the same or different; and a represents a mole fraction for the repeating unit and is in the range of from 50 to 97 mole %.

2. The water soluble polyimide resin according to claim 1, which number average molecular weight ranges from 10,000 to 300,000, as determined by Gel Permeation Chromatography (GPC) and converted into polystyrene.

3. The water soluble polyimide resin according to claim 1, which has an inherent viscosity (IV) ranging from 0.20~0.95 dL/g.

4. A method for preparing the water soluble polyimide resin consisting of a repeat unit (I) and a repeat unit (II) in a block or random arrangement,

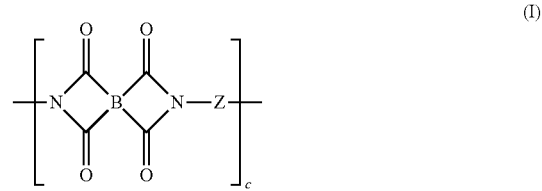

(I)

wherein B represents a tetravalent organic group; c represent a mole fraction for the repeating unit and is in the range of from 3 to 50 mole %; and Z represent a group of the following formula:

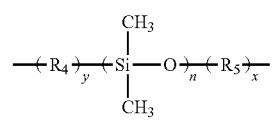

wherein $R_4$ and $R_5$ are the same or different, and each represents a alkylene group containing 1 to 6 carbon atoms, arylene group containing 6 to 20 carbon atoms, aralkylene containing 6 to 20 carbon atoms, or arylene-oxy-alkylene group containing 6 to 20 carbon atoms; n, x, and y each represents an integral more than or equal to 1;

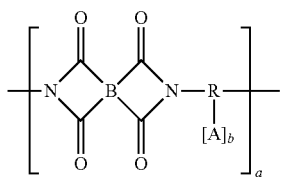

(II)

wherein B represents a tetravalent organic group; R represents a phenylene group; b represents a number of 1, or 2; A represents a group selected from —OH and —COOH, when b is the number of 2, the plural A's are each the same or different; and a represents a mole fraction for the repeating unit and is in the range of from 50 to 97 mole %;

said method comprises the following steps:

(a) reacting tetracarboxylic dianhydride, diamine having siloxane group, and diamine having a carboxyl and/or a hydroxyl group, to obtain a polyamic acid precursor having a carboxyl and/or a hydroxyl group; wherein the molar equivalent ratio of tetracarboxylic dianhydride to diamines is from 1:0.8 to 1:1.2, and the molar ratio of the diamine having siloxane group to the diamine having a carboxyl and/or a hydroxyl group is from 3:97 to 50:50;

(b) heating the polyamic acid precursor having a carboxyl and/or a hydroxyl group obtained in the step (a) to obtain the polyimide consisting of the repeat unit (I) and the repeat unit (II).

5. The method according to claim 4, wherein the step (a) is carried out by first reacting the diamine having siloxane group with tetracarboxylic anhydride in excess molar equivalent amount of tetracarboxylic anhydride, then reacting with the diamine having a carboxyl and/or a hydroxyl group.

6. The method according to claim 4, wherein the step (a) is carried out at a temperature of from room temperature to 90° C.

7. The method according to claim 4, wherein the tetracarboxylic anhydride is at least one selected from the group consisting of 2,2'-di(3,4-dicarboxyphenyl)hexafluoropropane dianhydride (6FDA), pyromellitic dianhydride (PMDA), 4,4'-oxydiphthalic anhydride (ODPA), 3,3',4,4'-biphenyl tetracarboxylic dianhydride (BPDA), 3,3',4,4'-benzophenone tetracarboxylic dianhydride(BTDA), ethylene tetracarboxylic dianhydride, butane tetracarboxylic dianhydride, cyclopentane tetracarboxylic dianhydride, 2,2',3,3'-benzophenone tetracarboxylic dianhydride, 2,2',3,3'-biphenyl tetracarboxylic dianhydride, 2,2-di(3,4-dicarboxyphenyl)hexafluoropropane dianhydride, 2,2-di(2,3-dicarboxylphenyl)propane dianhydride, di(3,4-dicarboxylphenyl)ether dianhydride, di(3,4-dicarboxylphenyl)sulfone dianhydride, 1,1-di(2,3-dicarboxylphenyl)ethane dianhydride, di(2,3-dicarboxylphenyl)methane dianhydride, di(3,4-dicarboxylphenyl)methane dianhydride, 4,4'-(p-phenyleneoxy)diphthalic dianhydride, 4,4'-(m-phenyleneoxy)diphthalic dianhydride, 2,3,6,7-naphthalenetetracarboxylic dianhydride, 1,4,5,8-naphthalenetetracarboxylic dianhydride, 1,2,5,6-naphthalenetetracarboxylic dianhydride, 1,2,3,4-benzenetetracarboxylic dianhydride, 3,4,9,10-perylenetetracarboxylic acid dianhydride, 2,3,6,7-anthracene-tetracarboxylic dianhydride and 1,2,7,8-Phenanthrene-tetracarboxylic dianhydride and their combination.

8. The method according to claim 4, wherein the diamine having a carboxyl and/or a hydroxyl group is at least one selected from the group consisting of 3,5-diamino-4-hydroxybenzoic acid, 3,5-diaminosalicylic acid, and 3,5-diaminobenzoic acid and their combination.

9. The method according to claim 4, wherein the diamine having siloxane group is at least one selected from the group consisting of 1,3-di(3-aminopropyl)-1,1,3,3-tetramethyldisiloxane(DSI), 1,3-di(4-aminobutyl)-1,1,3,3-tetramethyldisiloxane, 1,3-di(3-aminopropyl)-1,3-dimethyl-1,3-diphenyldisiloxane, 1,3-di(3-aminophenyl)-1,1,3,3-tetramethyldisiloxane, 1,3-di(4-aminophenyl)-1,1,3,3-tetramethyldisiloxane, 1,3-di(3-aminophenoxymethyl)-1,1,3,3-tetramethyldisiloxane, 1,3-di(4-aminophenoxymethyl)-1,1,3,3-tetra-methyldisiloxane, polysiloxane diamine having a molecular weight of 900 and their combination.

10. A water-soluble polyimide resin composition, which comprises (A) the water soluble polyimide resin according to claim 1; (B) (meth)acrylic acid monomer as a diluent; and (C) photo-initiator, wherein the weight ratio of the component (A): the component (B) is 100:10~200; the component (C) is present in amount of from 0.1~15.0% by weight based on the weight of the component (A).

\* \* \* \* \*